United States Patent
Ishitani et al.

(10) Patent No.: US 7,915,581 B2
(45) Date of Patent: Mar. 29, 2011

(54) METHODS FOR SAMPLE PREPARATION AND OBSERVATION, CHARGED PARTICLE APPARATUS

(75) Inventors: Tohru Ishitani, Hitachinaka (JP); Uki Kabasawa, Hitachinaka (JP); Tsuyoshi Ohnishi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 274 days.

(21) Appl. No.: 12/353,303

(22) Filed: Jan. 14, 2009

(65) Prior Publication Data
US 2009/0127458 A1     May 21, 2009

Related U.S. Application Data

(63) Continuation of application No. 11/482,094, filed on Jul. 7, 2006, now Pat. No. 7,482,586.

(30) Foreign Application Priority Data

Jul. 8, 2005 (JP) ................... 2005-200833

(51) Int. Cl.
  *G01N 23/00* (2006.01)
  *G21K 7/00* (2006.01)
  *A61N 5/00* (2006.01)
  *H01J 37/08* (2006.01)
(52) U.S. Cl. ..... 250/307; 250/306; 250/310; 250/492.1; 250/492.21
(58) Field of Classification Search ............... 250/306, 250/307, 310, 311, 492.1, 492.21, 492.3
See application file for complete search history.

(56) References Cited

U.S. PATENT DOCUMENTS

| | | | | |
|---|---|---|---|---|
| 5,929,983 A | * | 7/1999 | Lu | 356/138 |
| 5,986,264 A | | 11/1999 | Grunewald | |
| 6,181,474 B1 | | 1/2001 | Ouderkirk et al. | |
| 7,009,192 B2 | * | 3/2006 | Suzuki et al. | 250/491.1 |
| 7,154,106 B2 | | 12/2006 | Oi et al. | |
| 7,166,839 B2 | | 1/2007 | Tanaka et al. | |
| 7,323,697 B2 | | 1/2008 | Kaga et al. | |
| 2004/0251427 A1 | | 12/2004 | Suzuki et al. | |
| 2005/0161601 A1 | | 7/2005 | Kochi et al. | |
| 2005/0194535 A1 | * | 9/2005 | Noji et al. | 250/311 |
| 2006/0060781 A1 | * | 3/2006 | Watanabe et al. | 250/310 |
| 2006/0226376 A1 | * | 10/2006 | Fujii | 250/492.21 |
| 2008/0116376 A1 | | 5/2008 | Takane et al. | |

FOREIGN PATENT DOCUMENTS
JP  2006-294354 A  10/2006

OTHER PUBLICATIONS
Japanese Office Action dated Dec. 1, 2009 (Three (3) pages).

* cited by examiner

*Primary Examiner* — Robert Kim
*Assistant Examiner* — Brooke Purinton
(74) *Attorney, Agent, or Firm* — Crowell & Moring LLP (57) ABSTRACT

In an SEM observation in a depth direction of a cross section processed by repeated FIB cross-sectioning and SEM observation to correct a deviation in an observation field of view and a deviation in focus, are corrected, the deviations occurring when a processed cross section moves in the depth direction thereof; information on a height and a tilt of a surface of cross section processing area is calculated before the processing, the above information is used, the deviation in a field of view and the deviation in focus in SEM observation, which correspond to an amount of movement of the cross section at a time of the processing, are predicted, and the SEM is controlled based on the predicted values.

18 Claims, 5 Drawing Sheets

METHODS FOR SAMPLE PREPARATION AND OBSERVATION, CHARGED PARTICLE APPARATUS

CROSS REFERENCE TO RELATED APPLICATION

This application is a continuing application of U.S. application Ser. No. 11/482,094, filed Jul. 7, 2006, which claims priority under 35 U.S.C. §119 to Japanese Patent Application No. 2005-200833, filed Jul. 8, 2005, the entire disclosure of which are herein expressly incorporated by reference.

BACKGROUND OF THE INVENTION

1. Field of the Invention

The present invention relates to methods of: processing a continuous cross section in a local area of a sample surface of a semiconductor device, a new material or the like by using a focused ion beam (hereinafter referred to as an FIB); and observing the continuous cross section by using a scanning electron microscope (hereinafter referred to as an SEM) and the like. The present invention also relates to a charged particle beam apparatus used for the methods.

2. Description of the Related Art

In Kato and Otsuka [2003] *THE TRC NEWS, No. 84*, pp. 40-43, Toray Research Center, a dual beam apparatus is described in which both irradiation axes in an FIB system and an electron beam system cross at an acute angle, and in which an image of a single area can be displayed in the form of scanning images of the two beams, that is, an image taken by a scanning ion microscope (hereinafter referred to as an "SIM image") and an SEM image. As can be expected from the case of the electron beam system, by processing and forming a cross section with the FIB (which is hereinafter referred to as "FIB cross-sectioning"), observation of the processed cross section using the SEM (the observation with the SEM is hereinafter referred to as "SEM observation") can be performed without tilting a sample. By repeatedly performing the FIB cross-sectioning and the SEM observation, it is possible to accumulate sequentially cross-sectioned images in a depth direction of a processed surface. That is, three dimensional (hereinafter referred to as 3D) observation can be performed. In Japanese Patent No. 2852078, a technology is disclosed in which heights of a sample surface at a plurality of points are detected using a laser beam, and a tilt of the sample surface is calculated by using the information on heights at the plurality of points.

In the SEM observation in a depth direction of a processed cross section, by repeatedly performing the FIB cross-sectioning and the SEM observation, since the processed cross section moves in the depth direction, a deviation in an observation field of view and a deviation in focus occur in the SEM observation due to the movement of the processed cross section.

SUMMARY OF THE INVENTION

An object of the present invention is to provide a method by which a deviation in an observation field of view and a deviation in focus in the SEM observation are corrected, and the SEM observation is continuously performed.

As a method by which a field of view and a focus in an SEM observation are caused to track the move of a processed cross section, one may consider a method by which a structure, serving as a mark within a moving cross section of a sample, is searched and tracked so that the position of the field of view is corrected and automatic focusing is achieved by automatically adjusting a focus on a cross section under observation as needed. However, the correction of the position of the field of view and the automatic focusing described above require searching operations (operations in a control computer) to achieve optimum states, respectively. Since such searching operations generally need several seconds to several tens of seconds to be completed, it is not possible during this time to perform the SEM observation on the processed cross section which is in a correct field of view and in focus.

In the present invention, to solve the above problem, for example, a height to a surface of a cross section processing area and a slope of the surface are calculated in advance, and using the above information, a deviation in a field of view and a deviation in focus in an SEM observation, which correspond to an amount of movement of a cross section at a time of processing, are predicted and corrected. A tracking device of the present invention is one by which the field of view and the focus are controlled to come to a predicted state. Since an SEM is to only track a predicted state, FIB cross-sectioning and SEM observation on a processed cross section can be not only repeatedly but also simultaneously performed.

In methods of making and observing a sample of the present invention in which a cross section formed on a sample surface by processing the sample surface using, for example, an FIB is moved in a direction the cross section moves backward; the cross section is irradiated with an electron beam from a direction of an axis which obliquely crosses an irradiation axis of the FIB; and the sample cross section moving as above is observed with the SEM, tilting information on the sample surface is obtained; using an angle formed by an irradiation axis of the FIB and an irradiation axis of the electron beam and the tilting information on the sample surface, correction coefficients are obtained which correspond to an amount of movement of a field of view of the SEM and an amount of a deviation of a focus position of the same, the movement of a field of view and the deviation of a focus position occurring due to moving of the sample cross section at a time of processing the same; and the movement of a field of view and the deviation of a focus position of the SEM are corrected using the correction coefficients, and the field of view and the focus position are caused to track the moving of the sample cross section.

The tilting information on the sample surface is obtained by using a relationship between a coordinate position of an SIM image of a mark formed, for example, on the sample surface and a coordinate position of the SEM image of the same. In a rectangular coordinate system with an irradiation axis of the FIB set as a $Z_i$ axis and with a plane perpendicular to the $Z_i$ axis set as a $X_i Y_i$ plane, when setting an $X_i$ axis within a plane containing the irradiation axis of the FIB and the irradiation axis of the electron beam, the tilting information on the sample surface corresponds to tilting angles of the sample surface, the sample surface being tilted relative to the $X_i$ axis with respect to the $Y_i$ axis as an axis of rotation. The tilting angle is obtained by using positions of mark images in the SIM image observed for two marks having different $X_i$ axis directional components, positions of mark images in an SEM image observed for the two marks, and an angle formed by the irradiation axis of the FIB and the irradiation axis of the electron beam.

A charged particle beam apparatus of the present invention in which a cross section formed on a sample surface by processing the sample surface using the FIB is moved in a direction the cross section moves backward; and the sample cross section moving as above is observed with an SEM includes: a sample stage for holding a sample; an FIB system in which the FIB is irradiated on the sample held on the sample stage and a sample cross section is processed; an electron beam system having an irradiation axis which crosses an irradiation axis of the FIB on the sample; a detector for detecting a sample signal emitted from the sample due to an irradiation of the FIB or an electron beam; a displaying section for displaying an SIM image and/or an SEM image; and a beam control section for controlling the FIB system and the electron beam system. Further, in the charged particle beam apparatus of the present invention, the beam control section holds correction coefficients for an amount of movement of a field of view of the SEM and an amount of a deviation of a focus position of the same, the movement of a field of view and the deviation of a focus position occurring due to moving of the sample cross section at a time of processing the same; corrects the movement of a field of view and the deviation of a focus position of the SEM using the correction coefficients; and controls the field of view and the focus position to track the moving of the sample cross section.

The beam control section obtains the tilting information on the sample surface by using a relationship between a coordinate position of an SIM image of a mark formed on the sample surface and a coordinate position of a SEM image of the same; and can obtain the correction coefficients for the amount of movement of a field of view of the SEM and the amount of a deviation of a focus position of the same by using the angle formed by the irradiation axis of the FIB and the irradiation axis of the electron beam and the tilting information on the sample surface.

The present invention is capable of causing a field of view and a focus in an SEM observation to track a processed cross section even if the processed cross section moves in its depth direction during the repeated performing of FIB cross-sectioning and SEM observation of the processed cross section.

DETAILED DESCRIPTION OF THE PREFERRED EMBODIMENTS

Embodiments of the present invention are described hereinafter with reference to accompanying drawings.

First Embodiment

Figure 1:
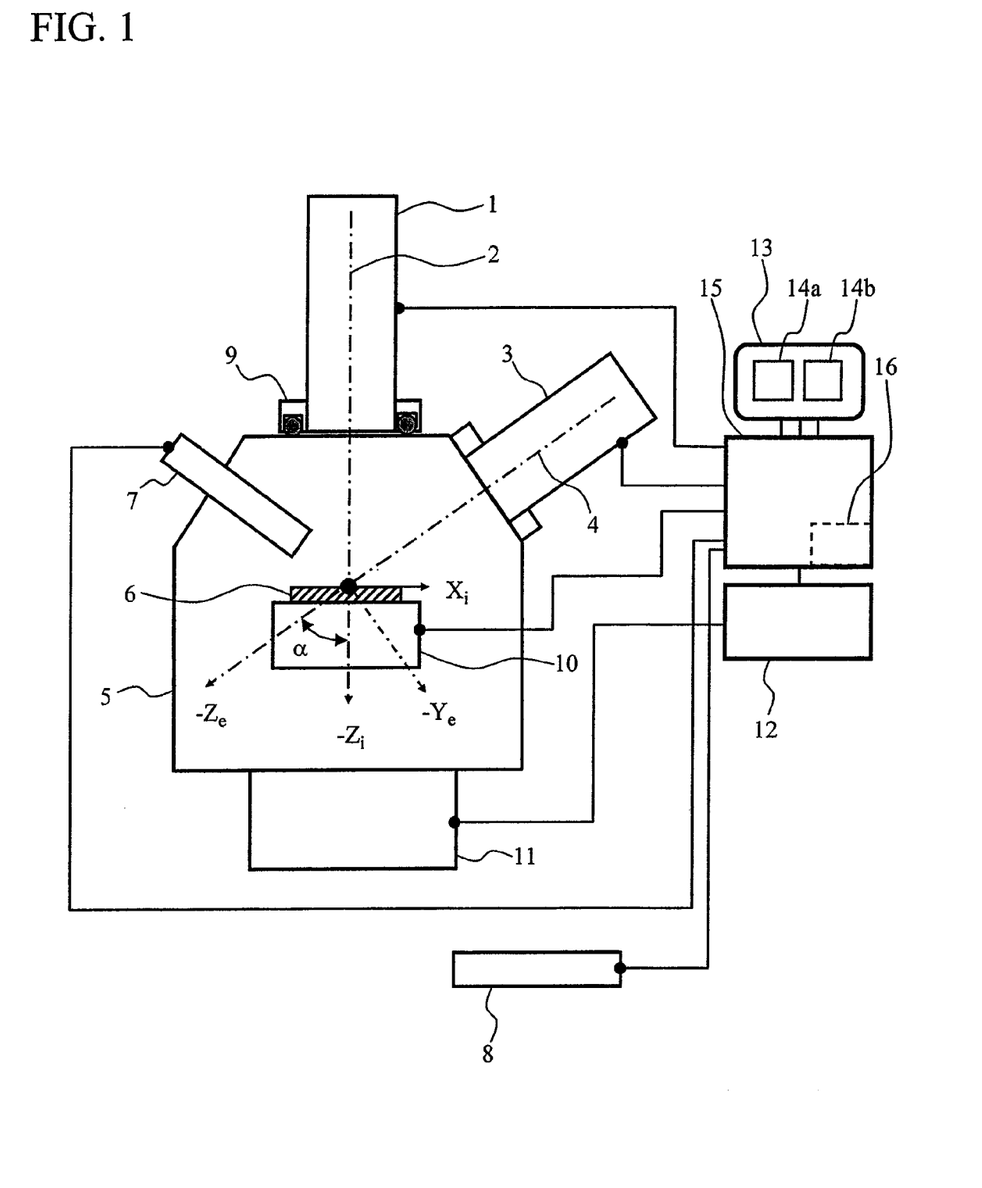
FIG. 1 is a schematic block diagram of a charged particle beam apparatus of the present invention.

Referring to FIGS. 1 to 4, an example of a constitution of a charged particle beam apparatus is described. FIG. 1 is a schematic block diagram of a charged particle beam apparatus of a first embodiment. Hereinafter, as coordinate systems for an FIB system 1, an electron beam system 3, and a sample 6, rectangular coordinate systems are adopted with coordinates (X, Y, Z) while the coordinates for the irradiation system 1, the irradiation system 3, and the sample 6 are differentiated from each other by attaching lower indices i, e, and s, respectively. The FIB system 1 and the electron beam system 3 are attached to a sample chamber 5, and an FIB irradiation axis $(-Z_i)$ and an electron beam irradiation axis $(-Z_e)$ cross over the sample 6 at an acute angle $\alpha$ (60 degrees in the present embodiment). The angle $\alpha$ at the above crossing is a fixed value determined by an apparatus and is known in advance. At this point of the crossing, coordinate origins $O_i$ and $O_e$ for the both coordinates are respectively set. For the sample coordinates, an $X_s$-$Y_s$ plane is put over a sample surface, and the coordinate axis $X_s$ is put within a plane spanned by two coordinate axes Zi and Ze. An origin $O_s$ is located so that the position thereof coincides with those of the origins $O_i$ and $O_e$.

Charged particles and an X-rays emitted from the sample are detected by a charged-particle detector 7 and an X-ray detector 8. Since the position of the X-ray detector 8 to be provided is hidden behind the electron beam system 3, the detector 8 is shown under the apparatus in FIG. 1 with that removed from the apparatus. An irradiation system position-adjusting section 9 is mechanically moved and adjusted in a plane parallel to an $X_i Y_i$ plane with the FIB system 1 put over the sample chamber 5, whereby the FIB irradiation axis 2 and the electron beam irradiation axis 4 approximately cross. In an adjustment carried out through a mechanical movement, there is a dislocation on the order of tens of microns left after completely crossing. This dislocation was eliminated by shifting at least one of beam deflection irradiation areas of an irradiation ion beam and an irradiation electron beam. The amount of the above shifting does not come into a transformation between coordinates of distance in the following respective coordinates. The sample 6 is mounted on a sample stage 10 on which the sample 6 is capable of moving (in the three directions of the $X_i$, $Y_i$, and $Z_i$-axes of the FIB system), rotating (with respect to the $Z_i$-axis as a rotational axis), and tilting (the $Y_i$-axis being a tilting axis). A surface of the sample 6 is adjusted to the crossing point (the origins $O_i$ and $O_e$) of the both irradiation axes as described above. A beam control section 15 controls irradiating, scanning, and the like of a an FIB and an electron beam, and further also controls imaging for an SEM image, an SIM image, and an X-ray image with charged particles, X-rays, and the like, which emit from the sample in synchronization with the scanning and which serve as luminance signals. These images are displayed on an image display device 13 along with a window image plane for a beam control. In the present embodiment in the drawing, an SIM image 14a and an SEM image 14b are displayed on the image display device 13. A vacuum pumping system 11 with which the sample chamber is evacuated is driven by a vacuum pumping system power. A SEM observation-field-of-view tracking section 16 to be described later is included in the beam control section 15.

Figure 2:
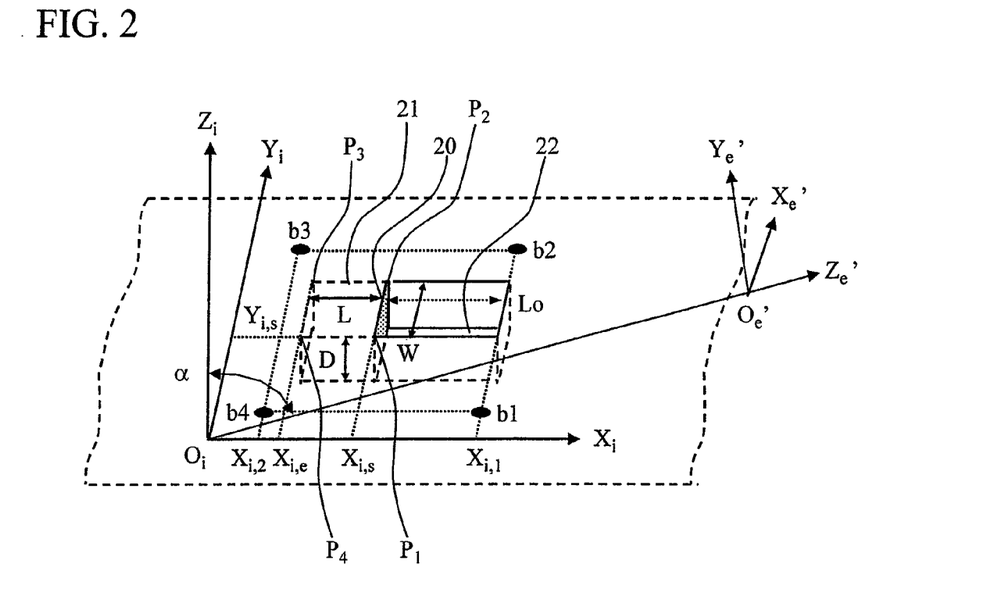
FIG. 2 is an explanatory view showing examples of a method of making a cross section sample using an FIB and that of performing an SEM observation (the case where a sample surface is flat, and consistent with an $X_i Y_i$ plane).
Figure 3:
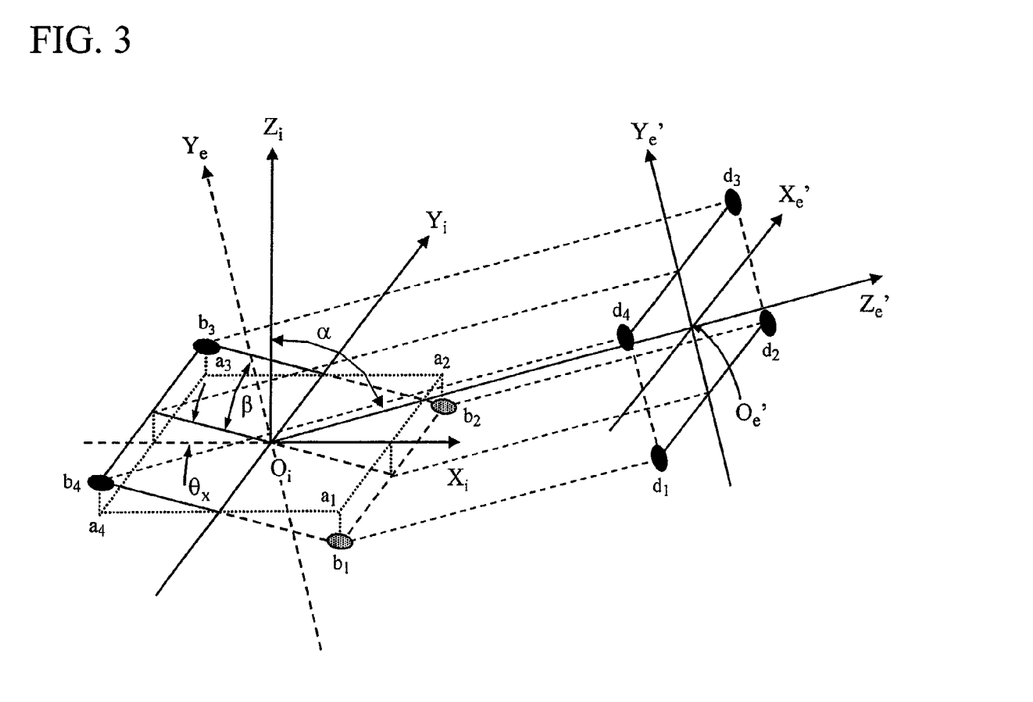
FIG. 3 is an explanatory view showing other examples of a method of making a cross section sample using an FIB and that of performing an SEM observation (the case where a to-be-analyzed surface of a sample is parallel to an $X_i$-axis and is tilted at an angle $\theta$ relative to the $X_i Y_i$ plane).
Figure 4:
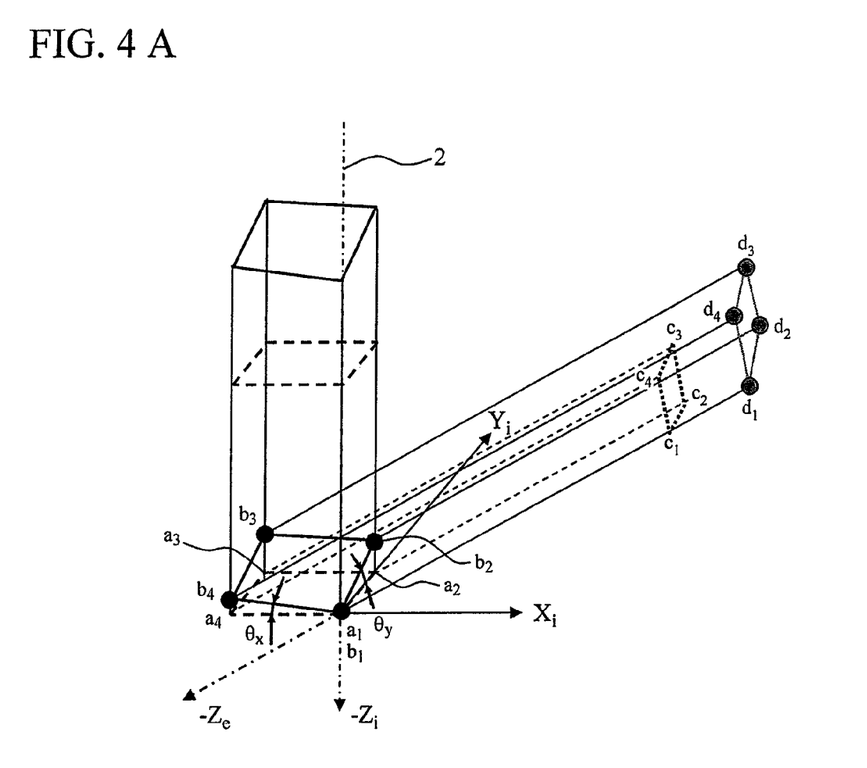
FIGS. 4A to 4C are explanatory views showing still other examples of a method of making a cross section sample using an FIB and that of performing an SEM observation (the case where although a to-be-analyzed surface of a sample can be approximated by a plane, it is not parallel to the $X_i$ and $Y_i$ axes and tilted relative to both axes at angles $\theta_x$ and $\theta_y$, respectively.)

FIGS. 2 to 4 are explanatory views for a method of making of a cross section sample using an FIB and for a method of performing SEM observation in the present embodiment. FIG. 2 is an aspect of the present embodiment in which a local observation surface ($X_s$-$Y_s$ plane) of the sample coincides with the $X_i Y_i$ plane of the ion irradiation system coordinates.

A region 21 of the sample on which a three dimensional (3D) analysis is intended to be performed is approximated by a rectangular parallelepiped having a width W, a depth D, and a length L, with a cross section 20 being an end. Typical sizes of W, D, and L are 8 μm, 8 μm, and 20 μm, respectively.

First, an FIB cross-sectioning is performed on a rectangular opening (width W, depth D, length Lo) 22 so that the cross section 20 is exposed. This cross section is an initial one on which an SEM observation is performed, and an observation field of view and a focus of an SEM image are adjusted to the above cross section. The cross section 20 is formed in a rigorous manner so that it is tilted at an angle of 1 to 3 degrees relative to a $Y_i$-$Z_i$ plane due to sputtering characteristics of ion. The rectangular opening 22 is used as an incidence path for an electron beam to perform the SEM observation on the cross section 20. Accordingly, the length Lo of the opening needs to be at least one on the order of D·tan α.

Next, to perform 3D observation, the processed cross section 20 is moved in a continuous or stepwise manner to $-X_i$ direction (in FIG. 2, $X_{i,s} \rightarrow X_{i,2}$) by a beam deflection shift in a scanning area of FIB cross-sectioning. When the amount of the movement is large, the field of view of the SEM observation is displaced to a large extent from the position $X_{i,s}$ of the cross section, resulting in an out-of-focus SEM image. A point of the present invention is that an observation field of view and a focus of an SEM image are caused to track a moving cross section as the cross section moves. To enable the above the tracking, amounts of correction for a deviation in an observation field of view and for a deviation in focus in the SEM observation, the amounts of which correspond to the amount of movement of the processed cross section, are measured prior to the operations of cross-sectioning and an observation, and an SEM state may be set as needed according to the above described amount of correction when performing an operation of cross-sectioning. A method of measuring the above amounts of correction is described, hereinafter.

In FIG. 2, when denoting the amount of movement of the cross section 20 as $\Delta X_i$ (>0), values $\Delta Y_e$ and $\Delta Z_e$ for movement are expressed as follows in terms of the crossing angle α, which is formed by the electron beam axis and the FIB axis in the electron beam coordinates.

$$\Delta Y_e = \cos \alpha \cdot \Delta X_i \qquad (1)$$

$$\Delta Z_e = -\sin \alpha \cdot \Delta X_i \qquad (2)$$

That is, as the amounts of correction for the observation field of view and the focus of the SEM observation, $\Delta Y_e$ and $\Delta Z_e$ calculated from the above respective equations may be set according to the amount of the beam deflection shift in the scanning area for FIB cross-sectioning.

In FIGS. 2 to 4, and FIG. 6, coordinate axes $X_e'$, $Y_e'$, and $Z_e'$ correspond to those obtained by moving the $X_e$, $Y_e$, and $Z_e$ axes in the electron beam system through the translating of the origin $O_e$ over the $Z_e$-axis. To avoid overlapping of an explanatory view on the $X_e Y_e$ plane and another view, a description is given by using the $X_e'$-$Y_e'$ plane which has been translated in parallel over the $Z_e$-axis. The $X_e Y_e$ plane and the $X_e'$-$Y_e'$ plane are completely equivalent. Further, to obtain information on the tilted angle of a local surface of a to-be-analyzed target portion, symbols $b_1$ to $b_4$ are provided as marks on a sample surface in the vicinity of the local area. These marks are formed on corners of a rectangle having edges which are parallel to the $X_i$ and $Y_i$ axes, as remains of FIB cross-sectioning or deposited layers having used FIB-assisted deposition. Symbols $a_1$ to $a_4$ are projections of $b_1$ to $b_4$ projected on the $X_i Y_i$ plane. Symbols $c_1$ to $c_4$ and $d_1$ to $d_4$ are projections of $a_1$ to $a_4$ and $b_1$ to $b_4$ projected on the $X_e Y_e$ plane (or $X_e'$-$Y_e'$ plane), respectively. As in Eqs. (1) and (2), when the $X_s$-$Y_s$ plane for the sample surface coincides with the $X_i Y_i$ plane, amounts of correction, $\Delta Y_e$ and $\Delta Z_e$, can be calculated even if there are no marks.

Next, referring to FIG. 3, a description is given for the case where a local surface of a to-be-analyzed target portion of the sample is in parallel to the $Y_i$-axis (i.e. a tilted angle $\theta_y = 0$ where $\theta_y$ denotes an angle tilted relative to the $Y_i$-axis) and is, however, tilted at a small angle $\theta_x$ relative to the $X_i$-axis. Since the tilted angle $\theta_x$ is an unknown value, it is necessary to find in advance the value of the tilted angle $\theta_x$ and seek in advance amounts of correction for a deviation of an observation field of view and for a deviation in focus in order to track the cross section 20 under the SEM observation. To find out the above tilted angle $\theta_x$, at least two different kinds of marks having different $X_i$ values are provided on a sample surface in the vicinity of the position of a sample cross section to be made. A local area on the sample to which the marks are provided can be approximated by a plane. FIG. 3 is an example in which four marks $b_1$ to $b_4$ are provided to a sample surface. Since a mark plane ($X_s$-$Y_s$ plane) is tilted at an angle $\theta_x$ relative to the XS-YS plane, when denoting as B an angle which is formed by the mark plane and the $Y_e$ axis in the electron beam coordinates, the following relationship between β, $\theta_x$ and α is established.

$$\beta = \alpha - \theta_x \qquad (3)$$

For the distance between the marks $b_1$ and $b_4$ on the sample (hereinafter the distance between marks is denoted with an underline, e.g., $\underline{b_1 b_4}$), and for the distances between the marks $\underline{a_1 a_4}$ and between the marks $\underline{d_1 d_4}$, in which, using an SIM image and an SEM image, correction is made with image magnification, and thereafter measurement is made. Then relationships among the above distances $\underline{b_1 b_4}$, $\underline{a_1 a_4}$ and $\underline{d_1 d_4}$ are respectively expressed by using $\theta_x$ and β as follows.

$$\underline{a_1 a_4} = \cos \theta_x \cdot \underline{b_1 b_4} \qquad (4)$$

$$\underline{d_1 d_4} = \cos \beta \cdot \underline{b_1 b_4} \qquad (5)$$

Using Eqs. (3) to (5), the following is obtained.

$$\cos(\alpha - \theta_x)/\cos \theta_x = \underline{d_1 d_4}/\underline{a_1 a_4} \qquad (6)$$

From the equation above, $\theta_x$ can be expressed by the following equation.

$$\theta_x = \arctan \left[ \{1 - (\underline{d_1 d_4}/\underline{a_1 a_4})/\cos \alpha\} \tan \alpha \right] \qquad (7)$$

Since the distances $\underline{d_1 d_4}$ and $\underline{a_1 a_4}$ are measured values obtained by using the both images, and α is a known value determined with a charged beam apparatus, the angle $\theta_x$ can be calculated using Eq. (7). As long as there are two marks having different $X_i$ values such as $b_1$ and $b_4$, $\theta_x$ can be calculated. That is, any other one of the marks $b_1$ and $b_3$, $b_2$ and $b_3$, and $b_2$ and $b_4$ may be accepted. This is because the distances of projected marks, $\underline{a_1 a_3}$, $\underline{a_2 a_3}$, and $\underline{a_2 a_4}$, the projected marks being projections of the above marks projected on the $X_i Y_i$ plane, have components in the direction of the $X_i$-axis which all coincide with the distance $\underline{a_1 a_4}$.

Using a calculated value $\theta_x$ obtained by Eq. (7), an amount of the movement of a field of view denoted as $\Delta Y_e$ and an amount of the deviation of a focus position denoted as $\Delta Z_e$ in the electron beam coordinates, the both amounts corresponding to the amount of movement of the cross section 20 denoted by $\Delta X_i$, are expressed by Eqs. (8) and (9) being similar to Eqs. (1) and (2), and are predictable in advance according to $\Delta X_i$ (while $\Delta X_e=0$).

$$\Delta Y_e = K_y \cdot \Delta X_i \quad (8)$$

$$\Delta Z_e = K_z \cdot \Delta X_i \quad (9)$$

where $$K_y = \cos(\alpha - \theta_x)/\cos \theta_x \quad (10)$$

$$K_z = -\sin(\alpha - \theta_x)/\cos \theta_x \quad (11)$$

Here, $K_y$ and $K_z$ respectively denote correction coefficients of $\Delta Y_e$ which is the amount of the movement of a field of view and $\Delta Z_e$ which is the amount of the deviation of a focus position. It is noted, in particular, that if $\theta_x$ is set as $\theta_x=0$ in Eqs. (8) and (9), these equations coincide with Eqs. (1) and (2). Moreover, $\Delta Z_i$ corresponding to $\Delta X_i$ is expressed as follows.

$$\Delta Z_i = \Delta X_i \cdot \tan \theta_x \quad (12)$$

Last, referring to FIG. 4, a description is given for the case where small tilted angle components to the $X_i$ and $Y_i$ axes on the local surface of the to-be-analyzed target portion of the sample are $\theta_x$ and $\theta_y$, respectively. FIG. 4A is a perspective diagram showing a relationship between the marks $b_1$ to $b_4$ formed on the sample surface and the respective coordinate systems. FIG. 4B is a diagram showing projected images of the marks $b_1$ to $b_4$ projected on the $X_iY_i$ plane. FIG. 4C is a diagram showing projected images of marks $a_1$ to $a_4$ and marks $b_1$ to $b_4$, all being projected on the $X_eY_e$ plane. As in the case of FIG. 3, the symbols $a_1$ to $a_4$ indicate projected positions (refer to FIG. 4B) of the marks $b_1$ to $b_4$ projected on the $X_iY_i$ plane; and the symbols $c_1$ to $c_4$ and $d_1$ to $d_4$ indicate projected positions (refer to FIG. 4C) of the symbols $a_1$ to $a_4$ and $b_1$ to $b_4$ projected on the $X_eY_e$ plane. Even if the symbols $a_1$ to $a_4$ form a rectangle, the symbols $b_1$ to $b_4$ and $d_1$ to $d_4$ form parallelograms because of the presence of the tilts $\theta_x$ and $\theta_y$. An angle $\theta_{e,y}$, which is formed by a tilt of a line segment $d_1d_4$ in an SEM image to the $X_e$-axis, has a relationship with $\theta_y$ as expressed by the following equation.

$$\theta_y = \arctan[\tan \theta_{e,y}/\sin \alpha] \quad (13)$$

Setting the positional coordinates of points $d_j$ (j=1 to 4) in an SEM image as $(X_{e,j}, Y_{e,j})$, $\tan \theta_{e,y}$ can be calculated by the following equation.

$$\tan \theta_{e,y} = (Y_{e,2} - Y_{e,1})/(X_{e,2} - X_{e,1}) \quad (14)$$

Here, since the distance ratio, $(Y_{e,2}-Y_{e,1})/(X_{e,2}-X_{e,1})$, corresponds to a distance ratio, $d_2c_2/c_2c_1$, in FIG. 4C, $\theta_y$ can be calculated by Eqs. (13) and (14). An amount of the movement of a field of view denoted as $\Delta Y_e$ and an amount of the deviation of a focus position denoted as $\Delta Z_e$ in the electron beam coordinates, the both amounts corresponding to the amount of movement of the cross section 20 denoted by $\Delta X_i$, are expressed by the same equations as Eqs. (8) and (9). $\theta_y$ is not included in equations for calculating $\Delta Y_e$ and $\Delta Z_e$. There need to be at least three out of the marks $b_1$ to $b_4$ in order to measure a local surface (a plane approximation) tilted in an arbitrary direction, i.e., $\theta_x$ and $\theta_y$. However, there needs to be a calculation of only $\theta_x$ in order to predict $\Delta Y_e$ and $\Delta Z_e$. Accordingly, it suffices if there are at least two marks having different $X_i$ values, i.e., a pair of marks out of $b_1$ and $b_4$, $b_1$ and $b_3$, $b_2$ and $b_3$, or $b_2$ and $b_3$. In a calculation of $\theta_x$, if the pair is $b_1$ and $b_4$, $\theta_x$ is the same as the one obtained by Eq. (7). For the other pairs (denoted as $b_i$, $b_j$ in general), if a component of the distance $a_ia_j$ in the $X_i$-direction and a component of the distance $d_id_j$ in the $Y_e$-direction are, respectively, expressed as $(a_ia_j)_x$ and $(d_id_j)_y$, these components can be measured. Accordingly, the following equation, which is equivalent to Eq. (7), may be used.

$$\theta_x = \arctan[\{1-((d_id_j)_y/(a_ia_j)_x)/\cos \alpha\}/\tan \alpha] \quad (15)$$

Next, a description is given for a procedure of 3D observation in which FIB cross-sectioning and SEM observation for observing a processed cross section are repeatedly (or sequentially) performed.

(i) Setting of a 3D Observation Target Area and Positional Adjustment of a Sample Stage A size (width W, depth D, length L) and a position of a 3D observation target area are determined, and the 3D observation target area is adjusted to the vicinity of an intersection of both beams by performing XYZ movement of a sample stage. Next, with a to-be-formed cross section placed parallel to the $X_iY_i$ plane, and with a $Y_i$ component of the cross section's movement set to the value 0, the sample stage is rotated so that the cross section moves in the direction of $-X_i$ axis.

(ii) Forming of Marks

Four marks are formed in the vicinity of (or to surround) a surface of a setting area in the 3D observation target area. Respective marks are formed at positions corresponding to corners of a rectangle on the $X_iY_i$ plane, edges of the rectangle being parallel to the $X_i$ and $Y_i$ axes. Although the number of marks is generally four, which is the same as the number of corners of a rectangle, it suffices if there are at least three marks out of the four marks. When a local surface of an observation area is in parallel to the $X_iY_i$ plane in particular, marks are not necessary. When the surface is slightly tilted only in a direction of the $X_i$ axis, it suffices if there are at least two marks having different $X_i$ values. Although the shape of the mark is normally a round-shaped opening, or a groove having an "X"-like shape or a "+"-like shape, being cut out by performing FIB cross-sectioning, it may be a deposited layer locally formed by performing an FIB-assisted deposition.

(iii) Registration of Positional Coordinates $(X_i, Y_i)$ of Formed Marks

Positional coordinates $(X_i, Y_i)$ of the formed marks are registered. When the marks are formed by performing FIB cross-sectioning, coordinate data in the cross-sectioning can be used as positional coordinates $(X_i, Y_i)$ of the marks.

(iv) Observation of an SEM Image of a Mark, and Registration of Positional Coordinates $(X_e, Y_e)$ thereof.

An SEM image of a mark is observed, and positional coordinates $(X_e, Y_e)$ thereof are registered.

(v) Calculation of Tilted Angles $\theta$ $(\theta_x, \theta_y)$ of a To-be-Observed Local Sample Surface Tilted angles $\theta$ $(\theta_x, \theta_y)$ are calculated using Eqs. (7), (13) and (14).

(vi) Calculation of Correction Coefficients $K_y$ and $K_z$

Correction coefficients $K_y$ and $K_z$ for an amount of the movement of a field of view, $\Delta Y_e$, and an amount of the deviation of a focus position, $\Delta Z_e$, are respectively calculated by using Eqs. (10) and (11).

(vii) Setting of Conditions of FIB Cross-Sectioning and a Movement Speed of the Cross Section FIB conditions (conditions of a beam diameter, a beam current, and irradiation) and a movement speed $V_t$ of the cross section are registered.

(viii) Setting of an Initial Value and a Final Value of $X_i$ on the Moving Cross Section An initial value $X_{i,s}$ and a final value $X_{i,e}$ of $X_i$ on the moving cross section are set.

(ix) Forming of a Start Cross Section

In an example of FIG. 2, a left end of the rectangular opening 22 is set in a position a little short of a position represented by the initial value $X_i$, $X_{i,s}$, for processing the rectangular opening. Then, the side surface of the opening is moved to the position represented by the value $X_{i,s}$ by processing the unprocessed portion up to the position represented by the value $X_{i,s}$ under the conditions of the FIB cross-sectioning and irradiation (or scanning). The side surface of the opening thus moved is a start cross section.

(x) Registration of Information of a Field of View and a Focus Position of an SEM Observation Image of a Start Cross Section An SEM observation image is adjusted to a start cross section under 3D observation, and start values $(X_{e,s}, Y_{e,s}, Z_{e,s})$ for information on an observation field of view $(X_e, Y_e)$ and that of focus position $Z_e$ are registered. Start values $(X_{i,s}, Y_{i,s})$ and final values $(X_{i,e}, Y_{i,e})$ for positional information $(X_i, Y_i)$ of a cross section formed by the FIB cross-sectioning are also registered. As the kind of signal for an observation image of an SEM cross section, at least one of secondary electrons, reflected electrons, and X-rays is selected, and registered along with the observation conditions. Then, the observation image of the start cross section is obtained and registered.

(xi) Moving-and-Processing of a Cross Section

A cross section is moved and processed using the FIB for processing which is registered in (vii) described above. Concurrently with the processing time t, an FIB irradiation area is moved in the $-X_i$ direction, and in synchronization therewith, the processed cross section is also moved. An amount of the movement (>0) is set as $\Delta X_i$. $\Delta X_i$ can be expressed by the product of the movement speed of a cross section Vs and the processing time $t [\Delta X_i = V_s \cdot t]$.

(xii) Calculation of Amount of Correction for Information of an Observation Field of View and a Focus Position in SEM Observation $\Delta Y_e$ and $\Delta Z_e$ of amounts of correction $(\Delta X_e, \Delta Y_e, \Delta Z_e)$ for information $(X_e, Y_e, Z_e)$ of an observation field of view and a focus position in an SEM observation are calculated using Eqs. (8) and (9), respectively. For correction coefficients $K_y$ and $K_z$, calculated values in (vi) are used. $\Delta X_e$ is constantly set to the value 0.

(xiii) Setting of Coordinates of an Observation Field of View and a Focus Position of an SEM Observation Image Coordinate values $(X_e + \Delta X_e, Y_e + \Delta Y_e, Z_e + \Delta Z_e)$ of an observation field of view and a focus position of an SEM observation image are set.

(xiv) Obtaining of SEM Observation Image

An observation image of an SEM cross section is obtained, and recorded as a function of an amount $\Delta X_i$ of movement of a cross section. Amounts of movement, $\Delta Y_i$ and $\Delta Z_i$, of the cross section in the $Y_i$ and $Z_i$ directions, which correspond to $\Delta X_i$, are, respectively, zero and an amount obtained by using Eq. (12) as a function of $\Delta X_i$.

(xv) End of Moving-and-Processing

When the processed cross section is moved to the final position $(X_i = X_{i,e})$ set in (viii), the operation of the moving-and-processing is terminated.

(xvi) 3D Analysis of SEM Images 3D images are generated using a sequence of SEM images of cross sections recorded in (xiii) as functions of the amounts of movement $(\Delta X_i, \Delta Y_i, \Delta Z_i)$ or $\Delta X_i$ of cross sections.

The SEM observation-field-of-view tracking section 16 includes beam control calculation software for achieving the processes (i) to (xv), and a process-observation flow display window. An example of items in the process-observation flowchart display window of the SEM observation-field-of-view tracking section 16 is shown in Table 1. The above described procedures for respective items are described in the column of Contents. Contents of the beam control calculation software are to execute calculations shown in the respective items of the procedures.

| Window Items | Contents |
|---|---|
| 1. Positional Adjustment of a Sample Stage | (i) Setting of a 3D Observation Target Area and Positional Adjustment of a Sample Stage |
| 2. Marking | (ii) Forming of Marks |
| | (iii) Registration of Positional Coordinates $(X_i, Y_i)$ of Formed Marks |
| 3. Observation of SEM Image | (iv) Observation of an SEM Image of a Mark, and Registration of Positional Coordinates $(X_e, Y_e)$ thereof |
| | (v) Calculation of Tilted Angles $\theta$ $(\theta_x, \theta_y)$ of a To-be-Observed Local Sample Surface |
| | (vi) Calculation of Correction Coefficients $K_y$ and $K_z$ |
| 4. Registration of Conditions of FIB Cross-Sectioning | (vii) Setting of Conditions of FIB Cross-Sectioning and a Movement Speed of the Cross-Section |
| | (viii) Setting of an Initial Value and a Final Value of $X_i$ on the Moving Cross Section |
| 5. Forming of Start Cross Section | (ix) Forming of a Start Cross Section |
| 6. Registration of Conditions of SEM Observation | (x) Registration of Information of a Field of View and a Focus Position of an SEM Observation Image of a Start Cross-Section |
| 7. Moving-and-Processing of Cross Section, and SEM Observation | (xi) Moving-and-Processing of a Cross Section |
| | (xii) Calculation of Amount of Correction for Information of an Observation Field of View and a Focus Position in SEM Observation |
| | (xiii) Setting of Coordinates of an Observation Field of View and a Focus Position of an SEM Observation Image |
| | (xiv) Obtaining of SEM Observation Image |
| 8. End of Moving-and-Processing | (xv) End of Moving-and-Processing |

A kind of luminance signal in an observation process of an SEM image of the above moving cross section is described. As the kind of signal, at least one of a secondary electron, a reflected electron, and an X-ray is selected. When using a secondary electron, since a secondary electron due to an FIB is mixed with a secondary electron due to an electron beam irradiation of an SEM, temporary interruption of an FIB irradiation is necessary while obtaining SEM images. That is, operations of FIB cross-sectioning and SEM observation were repeatedly performed. On the other hand, when using reflected electrons and X-rays for a luminance signal for SEM images, since there is no signal excitation due to an FIB irradiation, temporary interruption of an FIB irradiation was not necessary, and sequential operations of FIB cross-sectioning and SEM observation were performed.

Figure 6:
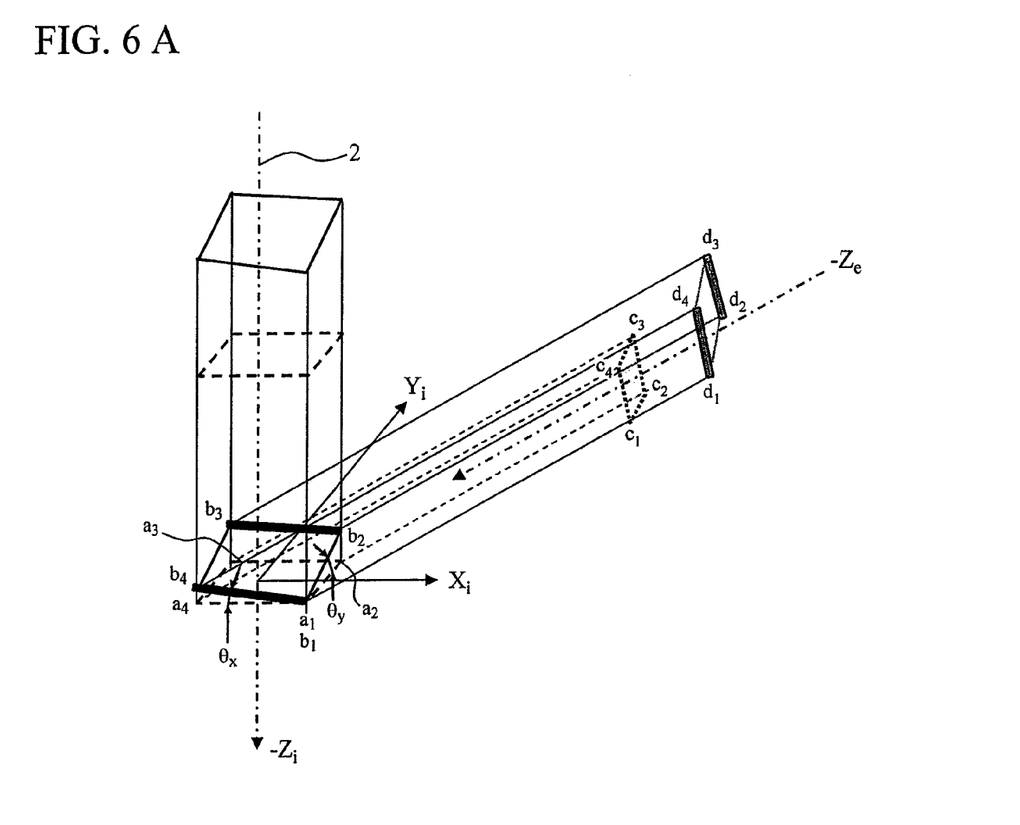
FIGS. 6A to 6C are explanatory views showing bar-like marks.

Referring to FIGS. 6A to 6C, other examples for the shapes of the marks are described. FIG. 6A is a perspective diagram showing relationships between marks $b_1$ to $b_4$ formed on a sample surface and the respective coordinate systems; FIG. 6B is a diagram showing projected images of the marks $b_1$ to $b_4$ projected on the $X_i Y_i$ plane; and FIG. 6C is a diagram showing projected images of marks $a_1$ to $a_4$ and the marks $b_1$ to $b_4$ projected on the $X_e Y_e$ plane. FIGS. 2, 3, and 4A to 4C are diagrams in the case where marks indicate respective representative positions, and are isolated. FIG. 6 shows an example in which at least two marks having different $X_i$ values are connected, substantially forming one mark. For example, two marks, $b_2$ and $b_3$, and $b_4$ and $b_1$, respectively having different $X_i$ values in FIG. 4 are respectively connected, resulting in bar-like marks $b_2b_3$ and $b_4b_1$ as shown in FIG. 6. The values $X_i$ at both ends of a single bar-like mark correspond to information on the $X_i$ values of respective marks. Accordingly, a mark may be one representing a single typical point, one bar-like mark representing two points, or one which is a combination of one mark and one bar-like mark.

Second Embodiment

Figure 5:
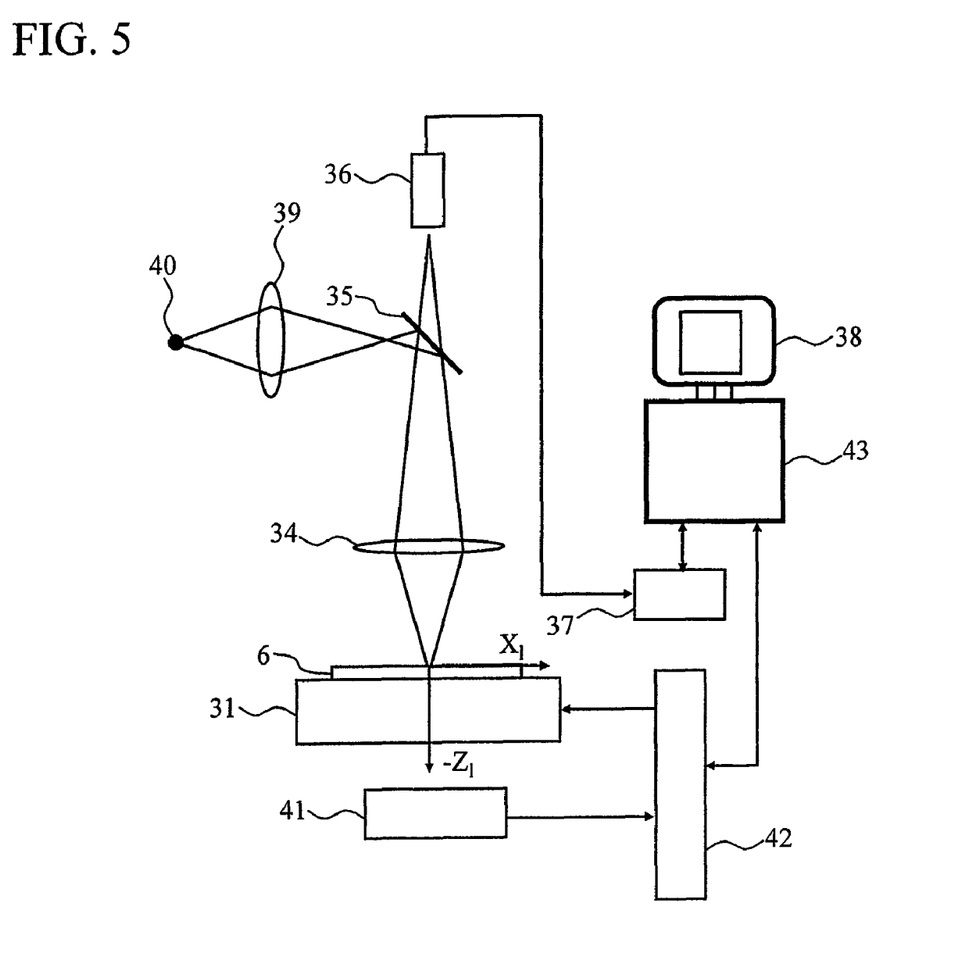
FIG. 5 is a diagrammatic view showing a measuring apparatus, in which a laser microscope is used and a height to a sample surface is denoted as Z.

Tilting information on a sample surface in a 3D observation target area can be obtained using a laser microscope. FIG. 5 is a diagrammatic view showing a measuring device, in which a laser microscope is used and a height to a sample surface is denoted as Z. A sample 6 is placed on a XYZ samples stage 31. A surface of the sample 6 is irradiated with illumination light from an illumination lamp 40 through a lens 39, a half mirror 35, and an objective lens 34. In the meantime, an image of the surface of the sample 6 is formed on an image pickup device 36 through the objective lens 34. An image signal from the image pickup device 36 is mirrored on a monitor device 38 through an image processing device 37. The image processing device 37, which is connected to a computer 43, outputs an image of the sample surface on the monitor device 38. The Z-axis of the XYZ stage 31 is moved up and down, and thereby an automatic focusing on the surface of the sample 6 is performed while viewing the monitor device 38. Reference numeral 41 denotes a displacement detector which reads an XYZ position of the XYZ stage 31, and a value in an XYZ coordinate system, which corresponds to an arbitrary position of the sample 6, is read into a computer 43 through an interface circuit 42. The XYZ stage 31 is controlled in response to a command from the computer 43 through the interface 42.

A 3D to-be-analyzed sample is placed on the XYZ stage so that $X_i$, $Y_i$, and $Z_i$ axes in a sectional view showing the making of a sample in FIG. 1 are consistent with X, Y, and Z axes on the sample stage. Accordingly, a specific part on the vicinity of a surface to be analyzed is kept being tracked by sequentially focusing the laser microscope on the specific part, and thereby coordinate values $(X_1, Y_1, Z_1)$ at that point are obtained and registered. Such coordinate position information includes tilting information on a sample surface to be analyzed. For example, denoting coordinates $(X_1, Y_1, Z_1)$ of a mark $b_j$ (=1 to 4) in FIG. 4A as $(X_{1j}, Y_{1j}, Z_{1j})$, $\theta_x$ and $\theta_y$ are respectively calculated by the following equations.

$$\theta_x = \arctan\left[(Z_{13}+Z_{14}-Z_{11}-Z_{12})/(X_{13}+X_{14}-X_{11}-X_{12})\right] \quad (16)$$

$$\theta_y = \arctan\left[(Z_{13}+Z_{14}-Z_{11}-Z_{12})/(X_{13}+X_{14}-X_{11}-X_{12})\right] \quad (17)$$

Accordingly, an amount of movement of a field of view $\Delta Y_e$ and an amount of deviation of a focus position $\Delta Z_e$ in electron beam coordinates, which correspond to an amount of movement $\Delta X_i$ of the cross section 20, can be calculated using Eqs. (8) to (11). The laser microscope and the charged particle beam apparatus are connected, and coordinate position information (or information on $\theta_x$ and $\theta y$) is sent from the laser microscope to a beam control section of the charged particle beam apparatus. In this case, the coordinate position information (or information on $\theta_x$ and $\theta_y$), which is obtained by the laser microscope, is read in through a recording medium, or it needs a key input by an operator, while the laser microscope and the charged particle beam apparatus may be in offline. When comparing with the method employing SIM images and SEM images as described above, the method using the laser microscope has a drawback that a laser microscope is necessary other than a charged particle beam apparatus integral with an SEM and an SIM.

What is claimed is:

1. Method of preparing and observing a sample in which a cross section formed on a sample surface is moved in a direction in which the cross section moves backward by processing the sample surface using a focused ion beam; in which an electron beam is irradiated on the cross section in a direction of an axis obliquely crossing an irradiation axis of the focused ion beam; and in which the moving sample cross section is observed with a scanning electron microscope, comprising:
    measuring an amount of correction for a deviation in focus in a scanning electron microscope observation, the amount of which corresponds to the amount of movement of the processed sample cross section, prior to the cross-sectioning and observation,
    setting a state of the scanning electron microscope according to the amount of correction when performing cross-sectioning, and
    causing the focus position of the scanning electron microscope to follow the movement of the sample cross section.

2. The method according to claim 1, wherein a secondary electron is used as a luminance signal for an image of the scanning electron microscope, and cross-sectioning with the focused ion beam and observations with the scanning electron microscope are repeatedly performed.

3. The method according to claim 1, wherein a reflected electron or an X-ray is used as a luminance signal for an image of the scanning electron microscope, and cross-sectioning with the focused ion beam and observations with the scanning electron microscope are sequentially performed.

4. Method of preparing and observing a sample in which a cross section formed on a sample surface is moved in a direction in which the cross section moves backward by processing the sample surface using a focused ion beam; in which an electron beam is irradiated on the cross section in a direction of an axis obliquely crossing an irradiation axis of the focused ion beam; and in which the moving sample cross section is observed with a scanning electron microscope, comprising:
    correcting a deviation of a focus position of the scanning electron microscope, which occurs due to the movement of the sample cross section by the processing with the focused ion beam, using information on an angle formed by the irradiation axis of the focused ion beam and the irradiation axis of the electron beam as well as tilting information on the sample surface, and
    causing the focus position of the scanning electron microscope to follow the movement of the sample cross section.

5. The method according to claim 4, wherein a secondary electron is used as a luminance signal for an image of the scanning electron microscope, and cross-sectioning with the focused ion beam and observations with the scanning electron microscope are repeatedly performed.

6. The method according to claim 4, wherein a reflected electron or an X-ray is used as a luminance signal for an image of the scanning electron microscope, and cross-sectioning with the focused ion beam and observations with the scanning electron microscope are sequentially performed.

7. Method of preparing and observing a sample in which a cross section formed on a sample surface is moved in a direction in which the cross section moves backward by processing the sample surface using a focused ion beam; in which an electron beam is irradiated on the cross section in a direction of an axis obliquely crossing an irradiation axis of the focused ion beam; and in which the moving sample cross section is observed with a scanning electron microscope, comprising:

correcting a deviation of a focus position of the scanning electron microscope, which occurs due to the movement of the sample cross section by the processing, using information on a height of a surface of a cross section processing area and tilting information on the surface, and causing the focus position of the scanning electron microscope to follow the movement of the sample cross section.

8. The method according to claim 7, wherein a secondary electron is used as a luminance signal for an image of the scanning electron microscope, and cross-sectioning with the focused ion beam and observations with the scanning electron microscope are repeatedly performed.

9. The method according to claim 7, wherein a reflected electron or an X-ray is used as a luminance signal for an image of the scanning electron microscope, and cross-sectioning with the focused ion beam and observations with the scanning electron microscope are sequentially performed.

10. A charged particle beam apparatus in which a cross section formed on a sample surface is movable in a direction in which the cross section moves backward by processing the sample surface using a focused ion beam; and in which the moving sample cross section is observed with a scanning electron microscope, comprising:

a sample stage for holding a sample;

a focused ion beam system for irradiating a focused ion beam on the sample held on the sample stage and for thus processing a sample cross section;

an electron beam system which has an irradiation axis crossing an irradiation axis of the focused ion beam on the sample;

a detector for detecting a sample signal emitted from the sample due to an irradiation of any one of the focused ion beam and an electron beam;

a displaying section for displaying at least one of a scanning ion microscope image and a scanning electron microscope image, the image or images being formed on the basis of detector output; and a beam control section for controlling the focused ion beam system and the electron beam system, wherein the apparatus is configured such that an amount of correction for a deviation in focus in a scanning electron microscope observation, the amount of which corresponds to the amount of movement of the processed sample cross section, is measured prior to the operation of the cross-sectioning and observation, a state of the scanning electron microscope is set according to the amount of correction when performing an operation of cross-sectioning, and the focus position of the scanning electron microscope is caused to follow the movement of the sample cross section.

11. The charged particle beam apparatus according to claim 10, wherein a secondary electron is used as a luminance signal for an image of the scanning electron microscope, and cross-sectioning with the focused ion beam and observations with the scanning electron microscope are repeatedly performed.

12. The charged particle beam apparatus according to claim 10, wherein a reflected electron or an X-ray is used as a luminance signal for an image of the scanning electron microscope, and cross-sectioning with the focused ion beam and observations with the scanning electron microscope are sequentially performed.

13. A charged particle beam apparatus in which a cross section formed on a sample surface is moved in a direction in which the cross section moves backward by processing the sample surface using a focused ion beam; and in which the moving sample cross section is observed with a scanning electron microscope, comprising:

a sample stage for holding a sample;

a focused ion beam system for irradiating a focused ion beam on the sample held on the sample stage, and for thus processing a sample cross section;

an electron beam system which has an irradiation axis crossing an irradiation axis of the focused ion beam on the sample;

a detector for detecting a sample signal emitted from the sample due to an irradiation of any one of the focused ion beam and an electron beam;

a displaying section for displaying at least one of a scanning ion microscope image and a scanning electron microscope image, the image or images being formed on the basis of detector output; and a beam control section for controlling the focused ion beam system and the electron beam system, wherein the apparatus is configured such that a deviation of a focus position of the scanning electron microscope, which occurs due to the movement of the sample cross section by the processing with the focused ion beam, is corrected using information on an angle formed by the irradiation axis of the focused ion beam and the irradiation axis of the electron beam as well as tilting information on the sample surface, and the focus position of the scanning electron microscope is caused to follow the movement of the sample cross section.

14. The charged particle beam apparatus according to claim 13, wherein a secondary electron is used as a luminance signal for an image of the scanning electron microscope, and cross-sectioning with the focused ion beam and observations with the scanning electron microscope are repeatedly performed.

15. The charged particle beam apparatus according to claim 13, wherein a reflected electron or an X-ray is used as a luminance signal for an image of the scanning electron microscope, and cross-sectioning with the focused ion beam and observations with the scanning electron microscope are sequentially performed.

16. A charged particle beam apparatus in which a cross section formed on a sample surface is moved in a direction in which the cross section moves backward by processing the sample surface using a focused ion beam; and in which the moving sample cross section is observed with a scanning electron microscope, comprising:

a sample stage for holding a sample;

a focused ion beam system for irradiating a focused ion beam on the sample held on the sample stage, and for thus processing a sample cross section;

an electron beam system which has an irradiation axis crossing an irradiation axis of the focused ion beam on the sample;

a detector for detecting a sample signal emitted from the sample due to an irradiation of any one of the focused ion beam and an electron beam;

a displaying section for displaying at least one of a scanning ion microscope image and a scanning electron microscope image, the image or images being formed on the basis of the detector output; and a beam control section for controlling the focused ion beam system and the electron beam system, wherein the apparatus is configured such that a deviation of a focus position of the scanning electron microscope, which occurs due to the movement of the sample cross section by the processing, is corrected using information on a height of a surface of a cross section processing area and tilting information on the surface, and the focus position of the scanning electron microscope is caused to follow the movement of the sample cross section.

17. The charged particle beam apparatus according to claim 16, wherein a secondary electron is used as a luminance signal for an image of the scanning electron microscope, and cross-sectioning with the focused ion beam and observations with the scanning electron microscope are repeatedly performed.

18. The charged particle beam apparatus according to claim 16, wherein a reflected electron or an X-ray is used as a luminance signal for an image of the scanning electron microscope, and cross-sectioning with the focused ion beam and observations with the scanning electron microscope are sequentially performed.

\* \* \* \* \*